United States Patent
Herth et al.

(10) Patent No.: US 11,344,364 B2
(45) Date of Patent: May 31, 2022

(54) SCREENING METHOD FOR A TARGET NERVE TO ABLATE FOR THE TREATMENT OF INFLAMMATORY LUNG DISEASE

(71) Applicant: Uptake Medical Technology Inc., Seattle, WA (US)

(72) Inventors: Felix J. F. Herth, Heidelberg (DE); Robert Barry, Seattle, WA (US); Erik Henne, Seattle, WA (US)

(73) Assignee: Uptake Medical Technology Inc., Seattle, WA (US)

( * ) Notice: Subject to any disclaimer, the term of this patent is extended or adjusted under 35 U.S.C. 154(b) by 374 days.

(21) Appl. No.: 16/107,342

(22) Filed: Aug. 21, 2018

(65) Prior Publication Data

US 2019/0069948 A1    Mar. 7, 2019

Related U.S. Application Data

(60) Provisional application No. 62/555,118, filed on Sep. 7, 2017.

(51) Int. Cl.
*A61B 18/14*    (2006.01)
*A61N 1/40*    (2006.01)
(Continued)

(52) U.S. Cl.
CPC .......... *A61B 18/1477* (2013.01); *A61B 18/04* (2013.01); *A61B 18/1492* (2013.01);
(Continued)

(58) Field of Classification Search
CPC . A61B 18/04; A61B 18/1477; A61B 18/1492; A61B 2018/00005;
(Continued)

(56) References Cited

U.S. PATENT DOCUMENTS

| 408,899 | A | 8/1889 | Small |
| 1,719,750 | A | 7/1929 | Bridge et al. |

(Continued)

FOREIGN PATENT DOCUMENTS

| AU | 721086 B2 | 6/2000 |
| EP | 1003582 B1 | 2/2003 |

(Continued)

OTHER PUBLICATIONS

Becker, et al.; Lung volumes before and after lung volume reduction surgery; Am J Respir Crit Care Med; vol. 157; pp. 1593-1599; (1998) Oct. 28, 1997.

(Continued)

*Primary Examiner* — Michael F Peffley
*Assistant Examiner* — Amanda L Zink
(74) *Attorney, Agent, or Firm* — Richard Batt (57) ABSTRACT

A screening method for identifying a target nerve to ablate in the treatment of inflammatory lung disease including chronic obstructive pulmonary disease and asthma. The method includes advancing a tool along the airway and into the vicinity of the candidate nerve. The candidate nerve is temporarily blocked or paralyzed. The patient is monitored for an adverse reaction during the step of temporarily blocking. If an adverse reaction is not observed, the candidate nerve is identified as the target nerve. In embodiments, the method further includes the step of ablating the target nerve.

12 Claims, 10 Drawing Sheets

(51) Int. Cl.
*A61B 18/04* (2006.01)
*A61B 18/00* (2006.01)

(52) U.S. Cl.
CPC .... *A61N 1/403* (2013.01); *A61B 2018/00005* (2013.01); *A61B 2018/00541* (2013.01); *A61B 2018/00577* (2013.01); *A61B 2018/048* (2013.01)

(58) Field of Classification Search
CPC ........... A61B 2018/00541; A61B 2018/00577; A61B 2018/048; A61N 1/403
See application file for complete search history.

(56) References Cited

U.S. PATENT DOCUMENTS

| | | | |
|---|---|---|---|
| 3,507,283 | A | 4/1970 | Thomas, Jr. |
| 3,880,168 | A | 4/1975 | Berman |
| 4,026,285 | A | 5/1977 | Jackson |
| 4,713,060 | A | 12/1987 | Riuli |
| 4,773,410 | A | 9/1988 | Blackmer et al. |
| 4,793,352 | A | 12/1988 | Eichenlaub |
| 4,915,113 | A | 4/1990 | Holman |
| 4,950,266 | A | 8/1990 | Sinofsky |
| 5,006,119 | A | 4/1991 | Acker et al. |
| 5,011,566 | A | 4/1991 | Hoffman |
| 5,084,043 | A | 1/1992 | Hertzmann et al. |
| 5,112,328 | A | 5/1992 | Taboada et al. |
| 5,158,536 | A | 10/1992 | Michael et al. |
| 5,263,951 | A | 11/1993 | Spears et al. |
| 5,331,947 | A | 7/1994 | Shturman |
| 5,334,190 | A | 8/1994 | Seiler |
| 5,348,551 | A | 9/1994 | Spears et al. |
| 5,352,512 | A | 10/1994 | Hoffman |
| 5,424,620 | A | 6/1995 | Cheon et al. |
| 5,462,521 | A | 10/1995 | Brucker et al. |
| 5,500,012 | A | 3/1996 | Brucker et al. |
| 5,503,638 | A | 4/1996 | Cooper et al. |
| 5,524,620 | A | 6/1996 | Rosenschein |
| 5,529,076 | A | 6/1996 | Schachar |
| 5,549,628 | A | 8/1996 | Cooper et al. |
| 5,562,608 | A | 10/1996 | Michael et al. |
| 5,575,803 | A | 11/1996 | Cooper et al. |
| 5,591,157 | A | 1/1997 | Hennings et al. |
| 5,620,440 | A | 4/1997 | Heckele et al. |
| 5,695,507 | A | 12/1997 | Auth et al. |
| 5,735,811 | A | 4/1998 | Brisken |
| 5,752,965 | A | 5/1998 | Francis et al. |
| 5,755,753 | A | 5/1998 | Knowlton |
| 5,779,642 | A * | 7/1998 | Nightengale ...... A61N 1/36021 600/461 |
| 5,782,914 | A | 7/1998 | Schankereli |
| 5,800,482 | A | 9/1998 | Pomeranz et al. |
| 5,824,703 | A | 10/1998 | Clark, Jr. |
| 5,827,268 | A | 10/1998 | Laufer |
| 5,913,856 | A | 6/1999 | Chia et al. |
| 5,957,919 | A | 9/1999 | Laufer |
| 5,964,752 | A | 10/1999 | Stone |
| 5,972,026 | A | 10/1999 | Laufer et al. |
| 5,986,662 | A | 11/1999 | Argiro et al. |
| 5,989,445 | A | 11/1999 | Wise et al. |
| 6,032,077 | A | 2/2000 | Pomeranz |
| 6,053,909 | A | 4/2000 | Shadduck |
| 6,059,011 | A | 5/2000 | Giolo |
| 6,083,255 | A | 7/2000 | Laufer et al. |
| 6,099,251 | A | 8/2000 | Lafleur |
| 6,102,037 | A | 8/2000 | Koch |
| 6,113,722 | A | 9/2000 | Hoffman et al. |
| 6,130,671 | A | 10/2000 | Argiro |
| 6,131,570 | A | 10/2000 | Schuster et al. |
| 6,139,571 | A | 10/2000 | Fuller et al. |
| 6,156,036 | A | 12/2000 | Sussman et al. |
| 6,162,232 | A | 12/2000 | Shadduck |
| 6,179,805 | B1 | 1/2001 | Sussman et al. |
| 6,194,066 | B1 | 2/2001 | Hoffman |
| 6,200,333 | B1 | 3/2001 | Laufer |
| 6,210,404 | B1 | 4/2001 | Shadduck |
| 6,219,059 | B1 | 4/2001 | Argiro |
| 6,273,907 | B1 | 8/2001 | Laufer |
| 6,283,988 | B1 | 9/2001 | Laufer et al. |
| 6,283,989 | B1 | 9/2001 | Laufer et al. |
| 6,299,633 | B1 | 10/2001 | Laufer |
| 6,300,150 | B1 | 10/2001 | Venkatasubramanian |
| 6,312,474 | B1 | 11/2001 | Francis et al. |
| 6,327,505 | B1 | 12/2001 | Medhkour et al. |
| 6,394,949 | B1 | 5/2002 | Crowley et al. |
| 6,398,759 | B1 | 6/2002 | Sussman et al. |
| 6,398,775 | B1 | 6/2002 | Perkins et al. |
| 6,409,723 | B1 | 6/2002 | Edwards |
| 6,411,852 | B1 | 6/2002 | Danek et al. |
| 6,458,231 | B1 | 10/2002 | Wapner et al. |
| 6,468,313 | B1 | 10/2002 | Claeson et al. |
| 6,488,673 | B1 | 12/2002 | Laufer et al. |
| 6,493,589 | B1 | 12/2002 | Medhkour et al. |
| 6,508,816 | B2 | 1/2003 | Shadduck |
| 6,527,761 | B1 | 3/2003 | Soltesz et al. |
| 6,575,929 | B2 | 6/2003 | Sussman et al. |
| 6,579,270 | B2 | 6/2003 | Sussman et al. |
| 6,585,639 | B1 | 7/2003 | Kotmel et al. |
| 6,588,613 | B1 | 7/2003 | Pechenik et al. |
| 6,589,201 | B1 | 7/2003 | Sussman et al. |
| 6,592,594 | B2 | 7/2003 | Rimbaugh et al. |
| 6,599,311 | B1 | 7/2003 | Biggs et al. |
| 6,610,043 | B1 | 8/2003 | Ingenito |
| 6,629,951 | B2 | 10/2003 | Laufer et al. |
| 6,652,594 | B2 | 11/2003 | Francis et al. |
| 6,653,525 | B2 | 11/2003 | Ingenito et al. |
| 6,669,694 | B2 | 12/2003 | Shadduck |
| 6,676,628 | B2 | 1/2004 | Sussman et al. |
| 6,679,264 | B1 | 1/2004 | Deem et al. |
| 6,682,520 | B2 | 1/2004 | Ingenito |
| 6,692,494 | B1 | 2/2004 | Cooper et al. |
| 6,712,812 | B2 | 3/2004 | Roschak et al. |
| 6,719,738 | B2 | 4/2004 | Mehier |
| 6,755,794 | B2 | 6/2004 | Soukup |
| 6,770,070 | B1 | 8/2004 | Balbierz |
| 6,776,765 | B2 | 8/2004 | Soukup et al. |
| 6,860,847 | B2 | 3/2005 | Alferness et al. |
| 6,885,888 | B2 | 4/2005 | Rezai |
| 6,901,927 | B2 | 6/2005 | Deem et al. |
| 6,904,909 | B2 | 6/2005 | Deem et al. |
| 6,907,881 | B2 | 6/2005 | Suki et al. |
| 6,911,028 | B2 | 6/2005 | Shadduck |
| 6,986,769 | B2 | 1/2006 | Nelson et al. |
| 6,997,189 | B2 | 2/2006 | Biggs et al. |
| 7,022,088 | B2 | 4/2006 | Keast et al. |
| 7,027,869 | B2 | 4/2006 | Danek et al. |
| 7,031,504 | B1 | 4/2006 | Argiro et al. |
| 7,083,612 | B2 | 8/2006 | Littrup et al. |
| 7,128,748 | B2 | 10/2006 | Mooradian et al. |
| 7,136,064 | B2 | 11/2006 | Zuiderveld |
| 7,144,402 | B2 | 12/2006 | Kuester et al. |
| 7,144,588 | B2 | 12/2006 | Nicholas et al. |
| 7,174,644 | B2 | 2/2007 | Critelli et al. |
| 7,175,644 | B2 | 2/2007 | Cooper et al. |
| 7,192,400 | B2 | 3/2007 | Campbell et al. |
| 7,198,635 | B2 | 4/2007 | Danaek et al. |
| 7,233,820 | B2 | 6/2007 | Gilboa |
| 7,235,070 | B2 | 6/2007 | Vanney |
| 7,335,195 | B2 | 2/2008 | Mehier |
| 7,347,859 | B2 | 3/2008 | Garabedian et al. |
| 7,412,977 | B2 | 8/2008 | Fields et al. |
| 7,422,563 | B2 | 9/2008 | Roschak et al. |
| 7,422,584 | B2 | 9/2008 | Loomas et al. |
| 7,425,212 | B1 | 9/2008 | Danek et al. |
| 7,462,162 | B2 | 12/2008 | Phan et al. |
| 7,628,789 | B2 | 12/2009 | Soltesz et al. |
| 7,708,712 | B2 | 5/2010 | Phan et al. |
| 7,740,017 | B2 | 6/2010 | Danek et al. |
| 7,756,563 | B2 | 7/2010 | Higgins et al. |
| 7,778,704 | B2 | 8/2010 | Rezai et al. |
| 7,815,590 | B2 | 10/2010 | Cooper |
| 7,819,908 | B2 | 10/2010 | Ingenito |
| 7,889,905 | B2 | 2/2011 | Higgins et al. |

(56) References Cited

U.S. PATENT DOCUMENTS

| | | | |
|---|---|---|---|
| 7,906,124 B2 | 3/2011 | Laufer et al. |
| 7,913,698 B2 | 3/2011 | Barry et al. |
| 7,985,187 B2 | 7/2011 | Wibowo et al. |
| 7,993,323 B2 | 8/2011 | Barry et al. |
| 8,002,740 B2 | 8/2011 | Willink et al. |
| 8,088,127 B2 | 1/2012 | Mayse et al. |
| 8,172,827 B2 | 5/2012 | Deem et al. |
| 8,187,269 B2 | 5/2012 | Shadduck et al. |
| 8,251,070 B2 | 8/2012 | Danek et al. |
| 8,292,882 B2 | 10/2012 | Danek et al. |
| 8,322,335 B2 | 12/2012 | Barry et al. |
| 8,409,167 B2 | 4/2013 | Roschak |
| 8,444,636 B2 | 5/2013 | Shadduck et al. |
| 8,585,645 B2 | 11/2013 | Barry et al. |
| 8,608,724 B2 | 12/2013 | Roschak |
| 8,628,495 B2 | 1/2014 | Horton et al. |
| 8,709,034 B2 | 4/2014 | Keast et al. |
| 8,734,380 B2 | 5/2014 | Barry et al. |
| 8,784,400 B2 | 7/2014 | Roschak |
| 8,858,549 B2 | 10/2014 | Shadduck et al. |
| 8,900,223 B2 | 12/2014 | Shadduck |
| 9,037,215 B2 | 5/2015 | Higgins et al. |
| 9,050,076 B2 | 6/2015 | Barry et al. |
| 9,133,858 B2 | 9/2015 | Macchia et al. |
| 9,265,468 B2 | 2/2016 | Rai et al. |
| 9,913,969 B2 | 3/2018 | Roschak |
| 10,064,697 B2 | 9/2018 | Sharma et al. |
| 2002/0077516 A1 | 6/2002 | Flanigan |
| 2002/0111386 A1 | 8/2002 | Michael et al. |
| 2002/0112723 A1 | 8/2002 | Schuster et al. |
| 2002/0177846 A1 | 11/2002 | Mulier et al. |
| 2003/0055331 A1 | 3/2003 | Kotmel et al. |
| 2003/0099279 A1 | 5/2003 | Venkatasubramanian et al. |
| 2003/0181922 A1 | 9/2003 | Alferness |
| 2003/0233099 A1 | 12/2003 | Danaek et al. |
| 2004/0031494 A1 | 2/2004 | Danek et al. |
| 2004/0038868 A1 | 2/2004 | Ingenito |
| 2004/0047855 A1 | 3/2004 | Ingenito |
| 2004/0055606 A1 | 3/2004 | Hendricksen et al. |
| 2004/0068306 A1 | 4/2004 | Shadduck |
| 2004/0199226 A1 | 10/2004 | Shadduck |
| 2004/0200484 A1 | 10/2004 | Springmeyer |
| 2004/0244803 A1 | 12/2004 | Tanaka |
| 2005/0016530 A1 | 1/2005 | Mccutcheon et al. |
| 2005/0066974 A1 | 3/2005 | Fields et al. |
| 2005/0166925 A1 | 8/2005 | Wilson et al. |
| 2005/0171396 A1 | 8/2005 | Pankratov et al. |
| 2005/0171582 A1 | 8/2005 | Matlock |
| 2005/0203483 A1 | 9/2005 | Perkins et al. |
| 2005/0215991 A1 | 9/2005 | Altman et al. |
| 2005/0222485 A1 | 10/2005 | Shaw et al. |
| 2006/0004400 A1 | 1/2006 | Mcgurk et al. |
| 2006/0047291 A1 | 3/2006 | Barry |
| 2006/0100619 A1 | 5/2006 | Mcclurken et al. |
| 2006/0130830 A1 | 6/2006 | Barry |
| 2006/0135955 A1 | 6/2006 | Shadduck |
| 2006/0162731 A1 | 7/2006 | Wondka et al. |
| 2006/0200076 A1 | 9/2006 | Gonzalez et al. |
| 2006/0224154 A1 | 10/2006 | Shadduck et al. |
| 2007/0032785 A1 | 2/2007 | Diederich et al. |
| 2007/0036417 A1 | 2/2007 | Argiro et al. |
| 2007/0068530 A1 | 3/2007 | Pacey |
| 2007/0091087 A1 | 4/2007 | Zuiderveld |
| 2007/0092864 A1 | 4/2007 | Reinhardt et al. |
| 2007/0102011 A1 | 5/2007 | Danek et al. |
| 2007/0106292 A1 | 5/2007 | Kaplan et al. |
| 2007/0109299 A1 | 5/2007 | Peterson |
| 2007/0112349 A1 | 5/2007 | Danek et al. |
| 2007/0118184 A1 | 5/2007 | Danek et al. |
| 2007/0137646 A1 | 6/2007 | Weinstein et al. |
| 2007/0293853 A1 | 12/2007 | Truckai et al. |
| 2008/0033493 A1 | 2/2008 | Deckman et al. |
| 2008/0132826 A1 | 6/2008 | Shadduck et al. |
| 2008/0249439 A1* | 10/2008 | Tracey ............... A61H 39/04 601/46 |
| 2009/0018538 A1 | 1/2009 | Webster et al. |
| 2009/0043301 A1 | 2/2009 | Jarrard et al. |
| 2009/0118538 A1 | 5/2009 | Pizzocaro et al. |
| 2009/0138001 A1 | 5/2009 | Barry et al. |
| 2009/0149846 A1 | 6/2009 | Hoey et al. |
| 2009/0149897 A1* | 6/2009 | Dacey, Jr. ............ A61M 35/10 607/3 |
| 2009/0156895 A1 | 6/2009 | Higgins et al. |
| 2009/0192508 A1 | 7/2009 | Laufer et al. |
| 2009/0216220 A1 | 8/2009 | Hoey et al. |
| 2009/0301483 A1 | 12/2009 | Barry et al. |
| 2009/0306640 A1 | 12/2009 | Glaze et al. |
| 2009/0306644 A1 | 12/2009 | Mayse et al. |
| 2009/0312753 A1 | 12/2009 | Shadduck |
| 2010/0094270 A1 | 4/2010 | Sharma |
| 2010/0204688 A1 | 8/2010 | Hoey et al. |
| 2010/0256714 A1 | 10/2010 | Springmeyer |
| 2010/0262133 A1 | 10/2010 | Hoey et al. |
| 2010/0310146 A1 | 12/2010 | Higgins et al. |
| 2011/0077628 A1 | 3/2011 | Hoey et al. |
| 2011/0118725 A1 | 5/2011 | Mayse et al. |
| 2011/0160648 A1 | 6/2011 | Hoey |
| 2011/0172654 A1 | 7/2011 | Barry et al. |
| 2011/0257644 A1* | 10/2011 | Barry ................... A61B 18/04 606/28 |
| 2011/0270031 A1 | 11/2011 | Frazier et al. |
| 2011/0301587 A1 | 12/2011 | Deem et al. |
| 2011/0319958 A1* | 12/2011 | Simon ................. A61N 2/006 607/42 |
| 2012/0016363 A1 | 1/2012 | Mayse et al. |
| 2012/0016364 A1 | 1/2012 | Mayse et al. |
| 2012/0289776 A1 | 11/2012 | Keast et al. |
| 2013/0006231 A1 | 1/2013 | Sharma et al. |
| 2013/0267939 A1 | 10/2013 | Barry et al. |
| 2013/0324987 A1* | 12/2013 | Leung ............... A61B 18/0218 606/20 |
| 2014/0025057 A1 | 1/2014 | Hoey et al. |
| 2014/0275952 A1 | 9/2014 | Monroe et al. |
| 2014/0276713 A1 | 9/2014 | Hoey et al. |
| 2015/0094607 A1 | 4/2015 | Barry et al. |
| 2015/0230852 A1 | 8/2015 | Barry et al. |
| 2016/0180529 A1 | 6/2016 | Rai et al. |
| 2016/0220297 A1 | 8/2016 | Kroon et al. |
| 2016/0287307 A1* | 10/2016 | Clark .................. A61B 5/4848 |
| 2016/0310200 A1 | 10/2016 | Wang |
| 2016/0374710 A1* | 12/2016 | Sinelnikov ........... A61B 8/481 600/439 |
| 2017/0172640 A1 | 6/2017 | Henne |
| 2018/0036084 A1* | 2/2018 | Krimsky ............... A61B 1/267 |
| 2018/0318002 A1 | 11/2018 | Barry et al. |
| 2019/0069948 A1 | 3/2019 | Herth et al. |
| 2019/0343579 A1* | 11/2019 | Tandri ................. A61B 18/02 |

FOREIGN PATENT DOCUMENTS

| | | |
|---|---|---|
| EP | 1143864 B1 | 2/2004 |
| EP | 1173103 B1 | 10/2005 |
| EP | 1326549 B1 | 12/2005 |
| EP | 1326548 B1 | 1/2006 |
| EP | 1485033 B1 | 8/2009 |
| WO | 0011927 A2 | 3/2000 |
| WO | 0102042 A1 | 1/2001 |
| WO | 02069821 A1 | 9/2002 |
| WO | 03070302 A1 | 8/2003 |
| WO | 03086498 A2 | 10/2003 |
| WO | 2005025635 A2 | 3/2005 |
| WO | 2005102175 A2 | 11/2005 |
| WO | 2006003665 A2 | 1/2006 |
| WO | 2006052940 A2 | 5/2006 |
| WO | 2006053308 A2 | 5/2006 |
| WO | 2006053309 A2 | 5/2006 |
| WO | 2006080015 A2 | 8/2006 |
| WO | 2006116198 A2 | 11/2006 |
| WO | 2008051706 A2 | 5/2008 |
| WO | 2009009236 A1 | 1/2009 |
| WO | 2009009398 A1 | 1/2009 |
| WO | 2009015278 A1 | 1/2009 |
| WO | 2009137819 A1 | 11/2009 |

(56) References Cited

FOREIGN PATENT DOCUMENTS

| WO | 2010042461 A1 | 4/2010 |
|---|---|---|
| WO | 2011056684 A2 | 5/2011 |
| WO | 2011060200 A1 | 5/2011 |
| WO | 2011060201 A1 | 5/2011 |
| WO | 2011127216 A2 | 10/2011 |

OTHER PUBLICATIONS

Blacker, G. F.; Vaporization of the uterus; J. of Obstetrics and Gynaecology; vol. 33; pp. 488-511; 1902.

Carpenter III et al.; Comparison of endoscopic cryosurgery and electrocoagulation of bronchi; Trans. Amer. Acad. Opth.; vol. 84; No. 1; pp. ORL-313-ORL-323; Jan. 1977.

Clinical trials.gov.; Study of the AeriSeal System for HyPerinflation Reduction in Emphysema; 4 pages; Nov. 5, 2014 retrieved from the internet (http://clinicaltrials.gov/show/NCT01449292).

Coda, et al., "Effects of pulmonary reventilation on gas exchange after cryolytic disobstruction of endobronchial tumors," Minerva Medical, vol. 72, pp. 1627-1631, Jun. 1981 (w/ Eng. Trans.).

Cox et al., "Bronchial Thermoplasty for Asthma." American Journal of Respiratory Critical Care Medicine 173: 965-969 (2006).

Delaunois; Anatomy and physiology of collateral respiratory pathways; Eur. Respir. J.; 2(9); pp. 893-904; Oct. 1989.

Eyal et al.; The acute effect of pulmonary burns on lung mechanics and gas exchange in the rabbit; Br. J. Anaesth.; vol. 47; pp. 546-552; (year of publication is sufficiently earlier than the effective U.S. filing date and any foreign priority date) 1975.

Ferlay et al.; GLOBOCAN 2008 v1.2, Cancer Incidence and Mortality Worldwide: IARC CancerBase No. 10 [internet] 16 pages; retrieved from the Internet (http://www.iarc.fr/en/media-centre/iarcnews/2010/GLOBOCAN2008.pdf); Lyon, France: International Agency for Research on Cancer; Jun. 1, 2010.

Fishman et al., A randomized trial comparing lung-volume-reduction surgery with medical therapy for severe emphysema, N Engl J Med, vol. 348, No. 21, pp. 2059-2073, May 22, 2003.

Goldberg et al.; Radiofrequency tissue ablation in the rabbit lung: Efficacy and complications; Acad. Radiol.; vol. 2; pp. 776-784; Sep. 1995.

Henne et al.; U.S. Appl. No. 14/957,433 entitled "Vapor treatment of lung nodules and tumors," filed Dec. 2, 2015.

Herth et al.; Efficacy predictors of lung volume reduction with zephyr valves in a european cohort; Eur. Respir. J.; 39(6); pp. 1334-1342; Jun. 2012.

Homasson, et al., "Bronchoscopic cryotherapy for airway strictures caused by tumors," Chest, vol. 90, No. 2, pp. 159-164, Aug. 1986.

Kang, Li, "Efficient optimal net surface detection for image segmentation—from theory to practice," M.Sc. Thesis, The University of Iowa, Dec. 2003.

Kinsella et al.; Quantitation of emphysema by computed tomography using a "densitymask" program and correlation with pulmonary function tests; Chest; 97(2); pp. 315-321; Feb. 1990.

Looga, R. U.; Mechanism of changes in the respiratory and cardiovascular reflexes from the lungs associated with intrapulmonary steam burns; Eng. Trans. from Byulleten Eksperimental noi Biologii I Meditsiny; vol. 61; No. 6; pp. 31-33; Jun. 1966.

Marasso, et al., "Cryosurgery in bronchoscopic treatment of tracheobronchial stenosis," Chest, vol. 103, No. 2, pp. 472-474, Feb. 1993.

Marasso, et al., "Radiofrequency resection of bronchial tumours in combination with cryotherapy: evaluation of a new technique," Thorax, vol. 53, pp. 106-109, (year of publication is sufficiently earlier than the effective U.S. filing date and any foreign priority date) 1998.

Mathur et al., Fiberoptic bronchoscopic cryotherapy in the management of tracheobronchial obstruction, Chest, vol. 110, No. 3, pp. 718-723, Sep. 1996.

Morice et al.; Endobrinchial argon plasma coagulation for treatment of hemotysis and neoplastic airway obstruction, Chest, vol. 119, No. 3, pp. 781-787, Mar. 2001.

Moritz et al.; The effects of inhaled heat on the air pasage and lungs; American Journal of Pathology; vol. XXI; pp. 311-331; (year of publication is sufficiently earlier than the effective U.S. filing date and any foreign priority date) 1944.

Moulding et al.; Preliminary studies for achieving transcervical oviduct occlusion by hot water or low-pressure steam Advances in Planned Parenthood; vol. 12, No. 2; pp. 79-85; (year of publication is sufficiently earlier than the effective U.S. filing date and any foreign priority date) 1977.

National Lung Screening Trial Research Team; Reduced lung-cancer mortality with low-dose computed tomographic screening; N. Eng. J. Med.; 365(5); pp. 395-409; Aug. 4, 2011.

Pieter et al.; U.S. Appl. No. 15/013,748 entitled "Medical vapor generator," filed Feb. 2, 2016.

Pracht, Adam, "VIDA takes new approach," Iowa City Press-Citizen, Sep. 12, 2005.

Quin, Jacquelyn, "Use of neodymium yttrium aluminum garnet laser in long-term palliation of airway obstruction," Connecticut Medicine, vol. 59, No. 7, pp. 407-412, Jul. 1995.

Sciurba et al.; A randomized study of endobronchial valves for advanced emphysema; N. Eng. J. Med.; 363(13); pp. 1233-1244; Sep. 23, 2010.

Shah et al.; Collateral ventilation and selection of techniques for bronchoscopic lung volume reduction; Thorax; 67(4); pp. 285-286; Apr. 2012.

Slebos et al.; Bronchoscopic lung volume reduction coil treatment of patients with severe heterogeneous emphysema; Chest; 142(3); pp. 574-582; Sep. 2012.

Sutedja, et al.; Bronchoscopic treatment of lung tumors; Elsevier, Lung Cancer, 11, pp. 1-17, Jul. 1994.

Tschirren et al.; Inlialhoracic airway trees: segmentation and airway morphology analysis from low-dose CT scans; IEEE Trans. Med. Imaging; vol. 24, No. 12; pp. 1529-1539; Dec. 2005.

Tschirren, Juerg; Segmentation, anatomical labeling, branchpoint matching, and quantitative analysis of human airway trees in volumetric CT images; Ph.D. Thesis; The University of Iowa; Aug. 2003.

Tschirren, Juerg; Segmentation, anatomical labeling, branchpoint matching, and quantitative analysis of human airway trees in volumetric CT images; Slides from Ph.D. defense; The University of Iowa; Jul. 10, 2003.

Van De Velde; Vapo-cauterization of the uterus; Amer. J. Med. Sci.; vol. CXVIII; (year of publication is sufficiently earlier than the effective U.S. filing date and any foreign priority date) 1899.

Vorre et al.; Morphology of tracheal scar after resection with CO2-laser and high-frequency cutting loop; Acta Otolaryngol (Stockh); vol. 107; pp. 307-312; (year of publication is sufficiently earlier than the effective U.S. filing date and any foreign priority date) 1989.

\* cited by examiner

SCREENING METHOD FOR A TARGET NERVE TO ABLATE FOR THE TREATMENT OF INFLAMMATORY LUNG DISEASE

CROSS-REFERENCE TO RELATED APPLICATIONS

This application claims the benefit of provisional patent application No. 62/555,118, filed Sep. 7, 2017, entitled "SCREENING METHOD FOR A TARGET NERVE TO ABLATE FOR THE TREATMENT OF INFLAMMATORY LUNG DISEASE", incorporated by reference herein in its entirety.

BACKGROUND OF THE INVENTION

The present invention relates to medical methods for treating inflammatory lung disease, and more specifically to minimally invasive medical methods for screening for nerves in the lung to ablate which are associated with airway function.

Chronic obstructive pulmonary disease (COPD) and asthma are lung inflammatory diseases and affect many people. Each disease is characterized by limited airflow, and interferes with normal breathing. Although COPD includes a number of diseases including chronic bronchitis and emphysema, it is generally characterized by airflow obstruction. People with airflow obstruction may have a number of symptoms including smooth muscle contraction, chronic cough with excess sputum production, and general thickening of the airway wall, all of which result in obstruction of normal breathing.

Various approaches to treat COPD and asthma include pharmacological treatment and interventional treatments.

Pharmacological treatment is an approach applied to most patients. For example, it is not uncommon for a physician to administer an inhaled bronchodilator (short or long acting) once or twice daily to relax and temporarily open airways. However, the side effects of the pharmacological agents include: nausea and vomiting, diarrhea, palpitations, a rapid heartbeat, an irregular heartbeat, headaches, and problems sleeping (insomnia), all of which are undesirable.

On the other hand, some patients are candidates for interventional treatments. An example of an interventional treatment includes application of radiofrequency energy through the airway wall to the nerve associated with contraction of the wall as described in U.S. Patent Publication No. 2013/0310822. See also, the Nuvaira™ Lung Denervation System (manufactured for clinical trial by Nuvaira, Inc., Minneapolis, Minn., USA, previously named Holaira, Inc.).

A challenge, however, in lung denervation therapy is to accurately identify and treat the nerve that is associated (or controls) the airway wall contraction. Identifying the wrong nerve to ablate can result in a number of non-beneficial or worse, adverse consequences. For example, should the wrong nerve be ablated, the airway obstruction remains unchanged following the procedure. The patient receives no clinical benefit while having had to undergo risk from the initial procedure. Additional procedures may be required, increasing patient risk.

What is more, significant adverse reactions can arise where the wrong nerve is inadvertently ablated. For example, where the targeted pulmonary parasympathetic nerve (PPN) and parasympathetic esophageal nerve (EPN) are intertwined, ablating the PPN can also ablate the EPN, causing inadvertent gastroparesis (paralysis of the esophagus and or stomach). Patients suffering from gastroparesis may require a permanent feeding tube. This is undesirable.

Accordingly, a method for assisting a physician to screen for target nerves to ablate for the treatment of lung inflammatory disease and that overcomes the above mentioned challenges is desirable.

SUMMARY OF THE INVENTION

The present invention is a method for screening for target nerves to ablate for the treatment lung inflammatory diseases including COPD and asthma.

In embodiments, a method temporarily blocks or paralyzes a candidate nerve for ablation, and monitors the patient's reaction to the temporary block. If the patient does not have an adverse reaction while being observed, the candidate nerve is identified as the target nerve to ablate.

In embodiments, the method further comprises probing or interrogating the candidate nerve for airway responsiveness. Probing is carried out prior to the temporary blocking. If the airway is responsive to the probing of the candidate nerve, the method proceeds to the temporary blocking or paralyzing step.

In embodiments, the temporary blocking or paralyzing step is performed using local anesthetic, cold therapy, or via physical force such as pinching or clamping.

In embodiments, the method further comprises ablating the target nerve after it has been identified. Ablation may be performed using a wide range of techniques including, for example, thermal vapor ablation.

In embodiments, the tool or instrument is advanced through a bronchoscope.

In embodiments, the tool or instrument is a transbronchial needle.

In embodiments the candidate nerve is a pulmonary parasympathetic nerve.

Still other descriptions, objects and advantages of the present invention will become apparent from the detailed description to follow, together with the accompanying drawings.

DETAILED DESCRIPTION OF THE INVENTION

Before the present invention is described in detail, it is to be understood that this invention is not limited to particular variations set forth herein as various changes or modifications may be made to the invention described and equivalents may be substituted without departing from the spirit and scope of the invention. As will be apparent to those of skill in the art upon reading this disclosure, each of the individual embodiments described and illustrated herein has discrete components and features which may be readily separated from or combined with the features of any of the other several embodiments without departing from the scope or spirit of the present invention. In addition, many modifications may be made to adapt a particular situation, material, composition of matter, process, process act(s) or step(s) to the objective(s), spirit or scope of the present invention. All such modifications are intended to be within the scope of the claims made herein.

Methods recited herein may be carried out in any order of the recited events which is logically possible, as well as the recited order of events. Furthermore, where a range of values is provided, it is understood that every intervening value, between the upper and lower limit of that range and any other stated or intervening value in that stated range is encompassed within the invention. Also, it is contemplated that any optional feature of the inventive variations described may be set forth and claimed independently, or in combination with any one or more of the features described herein.

All existing subject matter mentioned herein (e.g., publications, patents, patent applications and hardware) is incorporated by reference herein in its entirety except insofar as the subject matter may conflict with that of the present invention (in which case what is present herein shall prevail).

Reference to a singular item, includes the possibility that there are plural of the same items present. More specifically, as used herein and in the appended claims, the singular forms "a," "an," "said" and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

Figure 1A:
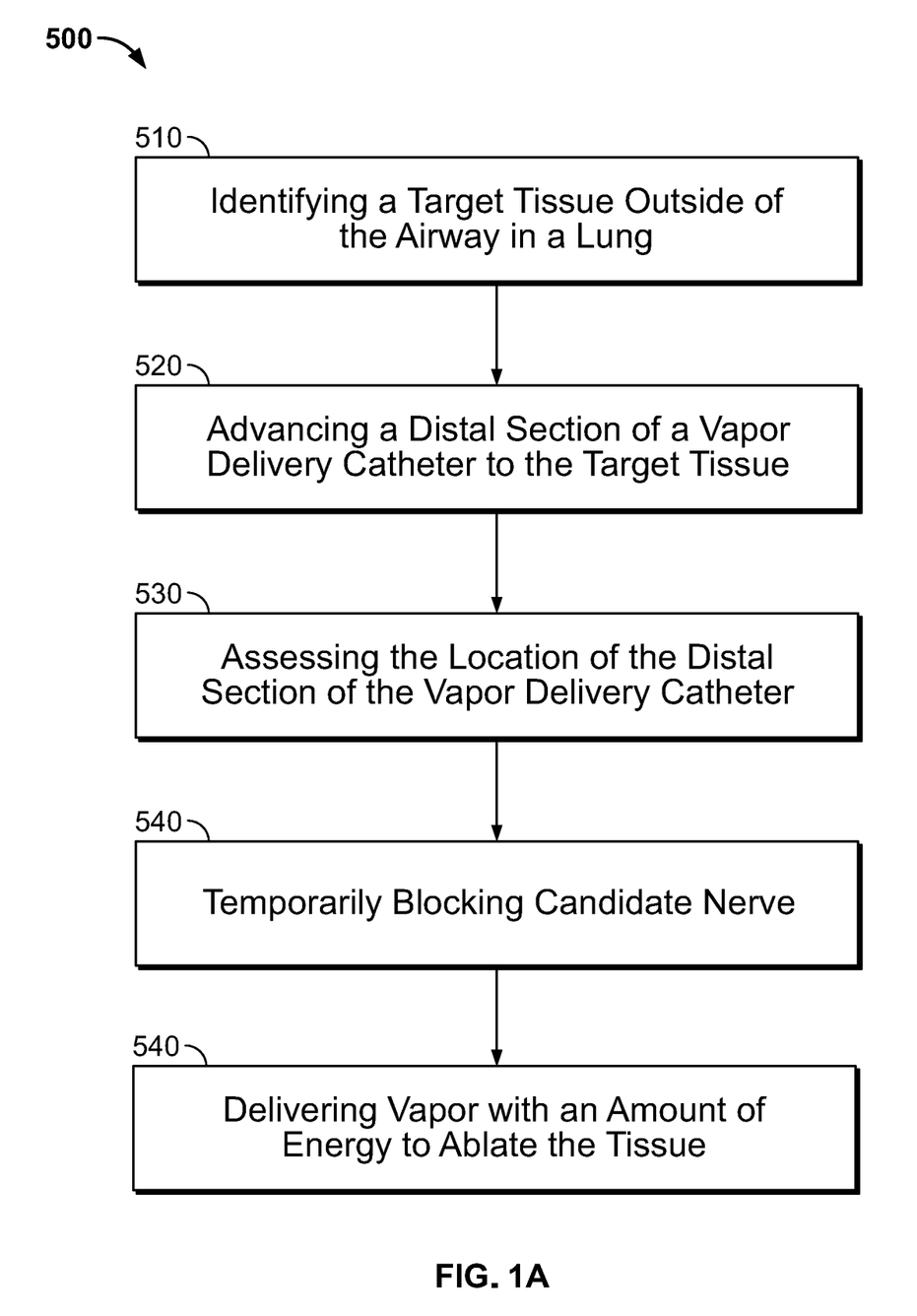
FIG. 1A is a flowchart of a method for treating lung inflammatory disease.

FIG. 1A is a flowchart of an overview of a method 500 for treating COPD or asthma.

Step 510 states to identify a target tissue outside of the airway in a lung for the treatment of lung inflammatory disease. As described herein, examples of target tissue include a nerve and airway smooth muscle. Noninvasive means may be applied to view and identify the target.

Step 520 states to advance a distal section of a vapor delivery catheter to the target tissue. In embodiments, the catheter comprises a working or access lumen and a sharpened tip which is adapted to penetrate the airway wall, creating an opening through the airway wall. The tip is further advanced through the wall, outside of the airway, and towards the target tissue.

Step 530 states to assess the location of the distal section of the catheter. Assessing may be performed by determining whether the distal section is in contact with the target tissue to be ablated using a number of different techniques as described herein. In embodiments, confirmation of the location of the distal section of the vapor delivery catheter is performed by probing the target tissue with the catheter and visually observing movement of the tissue structure commanded by the nerve. However, as described herein, a wide variety of techniques may be employed to assess the location of the vapor delivery catheter.

Step 540 states to temporarily block or screen the candidate nerve prior to the step of ablation to confirm that an adverse reaction shall not result from the ablation. The catheter may be activated to temporarily paralyze the candidate nerve, or another tool or instrument may be advanced through the catheter or sheath, or interchanged therewith to temporarily block the candidate nerve. As described further herein, temporarily blocking or paralyzing the nerve demonstrates whether ablating the candidate nerve has a clinical benefit, or causes an adverse reaction.

Step 550 states to deliver vapor with an amount of energy to ablate the tissue. The vapor follows the boundary of the airway, raising the temperature uniformly across the target tissue as opposed to developing a large temperature gradient. Ablating the target tissue (e.g., the nerve and/or smooth muscles surrounding the airway) serves to alleviate the conditions associated with COPD and asthma as described herein.

In embodiments, the catheter may be moved to additional target locations along the airway, or a different airway and the procedure repeated.

Additionally, in embodiments, the location of the catheter is assessed, and if the catheter is not in proper position, the catheter is further manipulated and the step of assessing is repeated. The process may be repeated until the catheter is ultimately in the desired position.

Figure 1B:
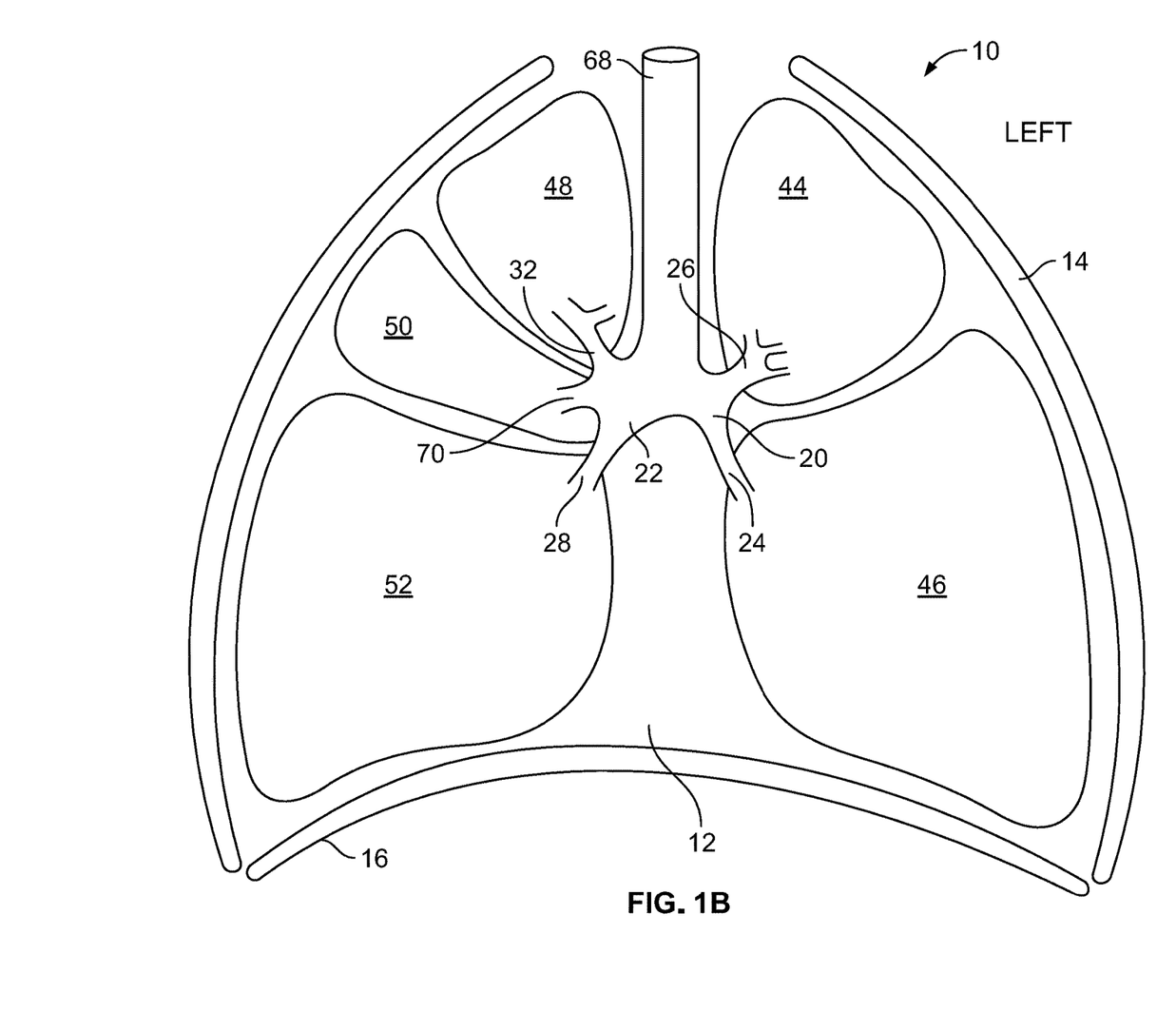
FIG. 1B illustrates a human respiratory system.

Now, with reference to FIG. 1B, pertinent anatomy is shown and described serving to facilitate understanding of the invention. Particularly, FIG. 1B illustrates a human respiratory system 10. The respiratory system 10 resides within the thorax 12 that occupies a space defined by the chest wall 14 and the diaphragm 16. The human respiratory system 10 includes left lung lobes 44 and 46 and right lung lobes 48, 50, and 52.

The respiratory system 10 may be characterized by a tree-like structure formed of branched airways including the trachea 68; left and right main stem bronchus 20 and 22 (primary, or first generation) and lobar bronchial branches 24, 26, 28, 32, and 70 (second generation). Segmental and subsegmental branches further bifurcate off the lobar bronchial branches (third and fourth generation). Each bronchial branch and sub-branch communicates with a different portion of a lung lobe, either the entire lung lobe or a portion thereof.

Figure 2A:
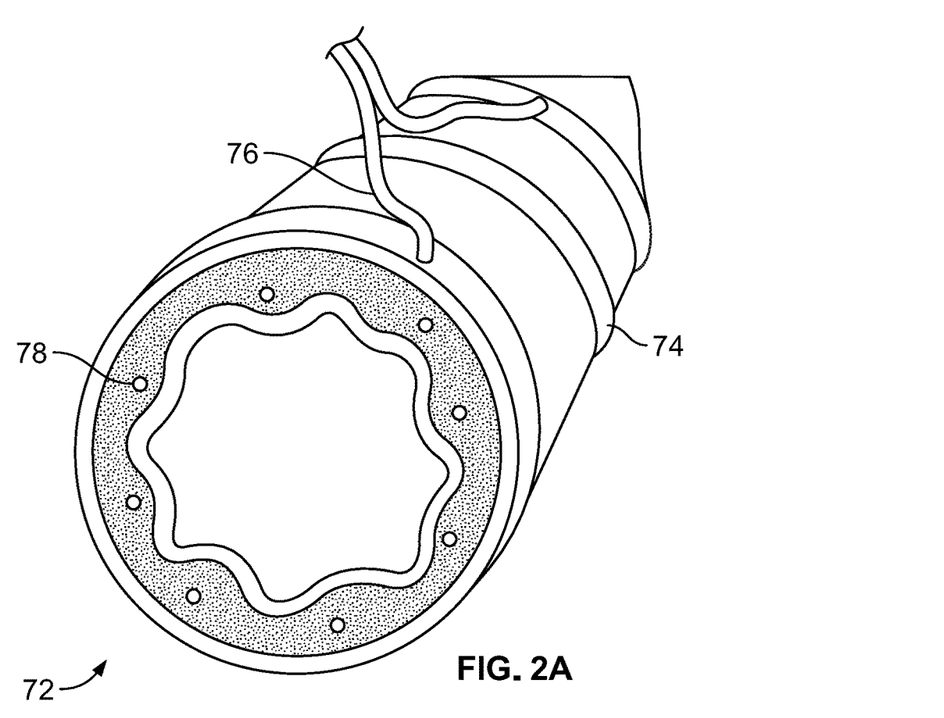
FIGS. 2A, 2B illustrate an airway in the respiratory system in a normal and asthmatic state respectively.
Figure 2B:
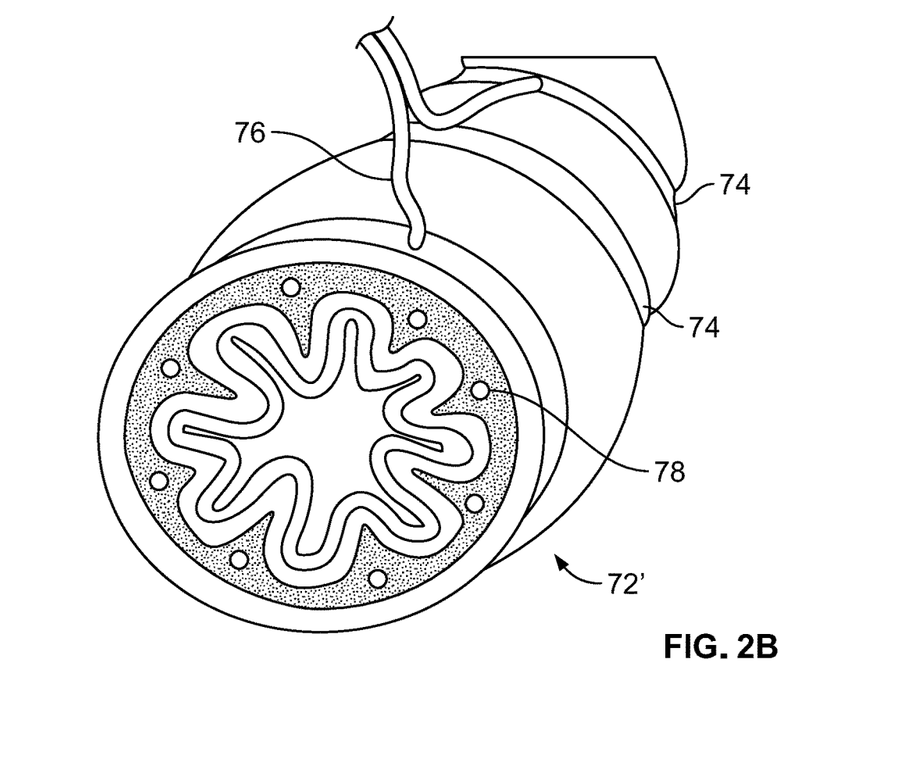

FIGS. 2A, 2B illustrate cross sectional views of an airway in a normal state 72 and asthmatic state 72', respectively. Smooth muscles 74 are shown axially spaced along the airway and are contracted in the asthmatic airway 72'. Nerves 76 communicate with the smooth muscles, and control movement of the smooth muscles 74. Thus, the nerves can affect the size or diameter of the airway passageway by causing the smooth muscles to constrict or expand. Blood vessels 78 are also shown in FIGS. 2A, 2B serving to transport blood therethrough.

Bronchoscopy Approach

Figure 3:
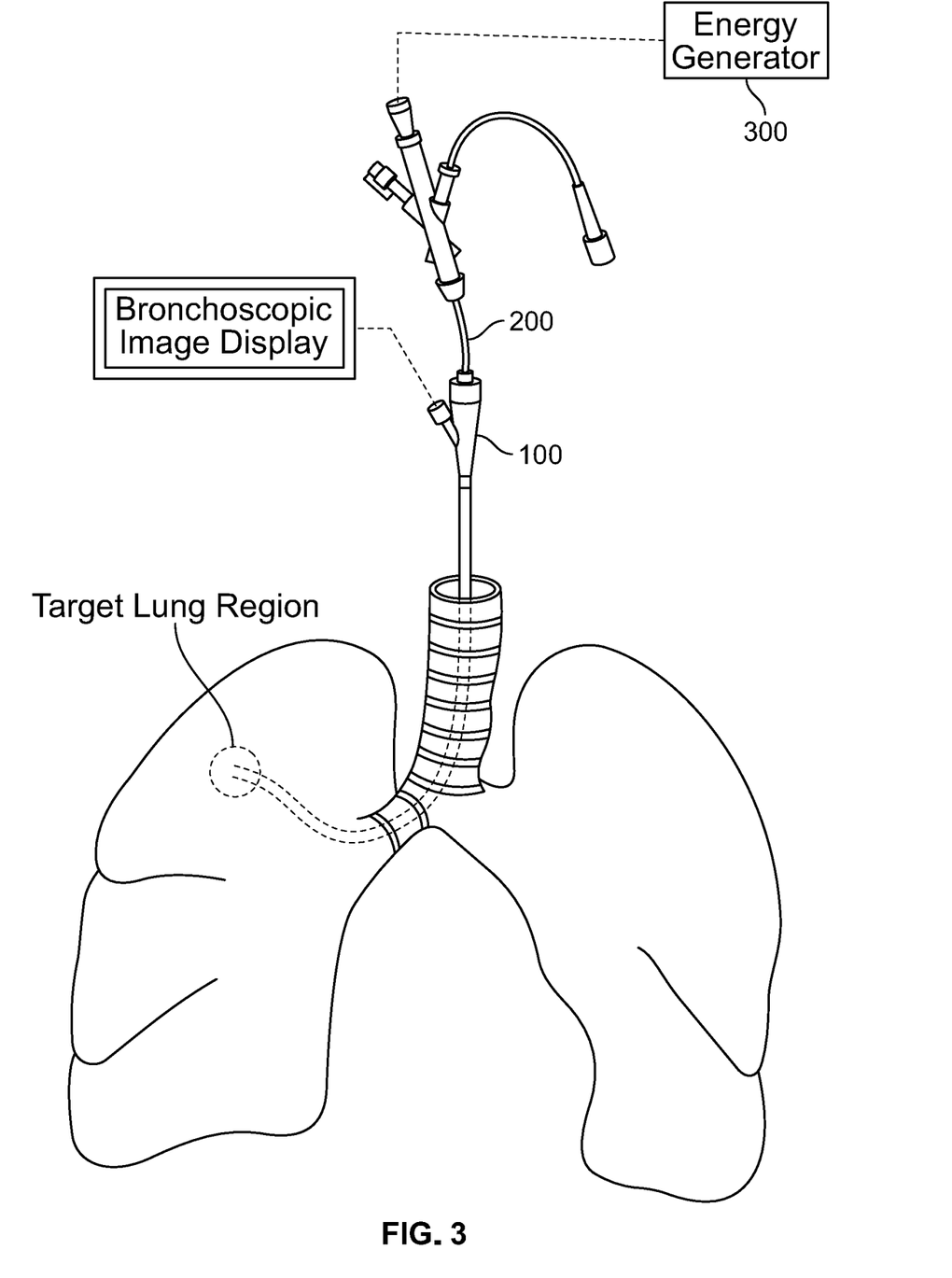
FIG. 3 illustrates a bronchoscopic method for treating lung tissue.

FIG. 3 illustrates a bronchoscopic procedure in accordance with some embodiments of the present invention. FIG. 3 shows a bronchoscope 100 having a working channel into which an energy delivery catheter 200 (or another tool) is inserted. Bronchoscope 100 is inserted into a patient's lungs while the proximal portion of the energy delivery catheter 200 remains outside of the patient. Energy delivery catheter 200 is adapted to operatively couple to an energy generator 300 as further discussed below. Examples of energy delivery catheters include, without limitation, a condensable vapor ablation catheter as described herein.

Energy Generator

Figure 4:
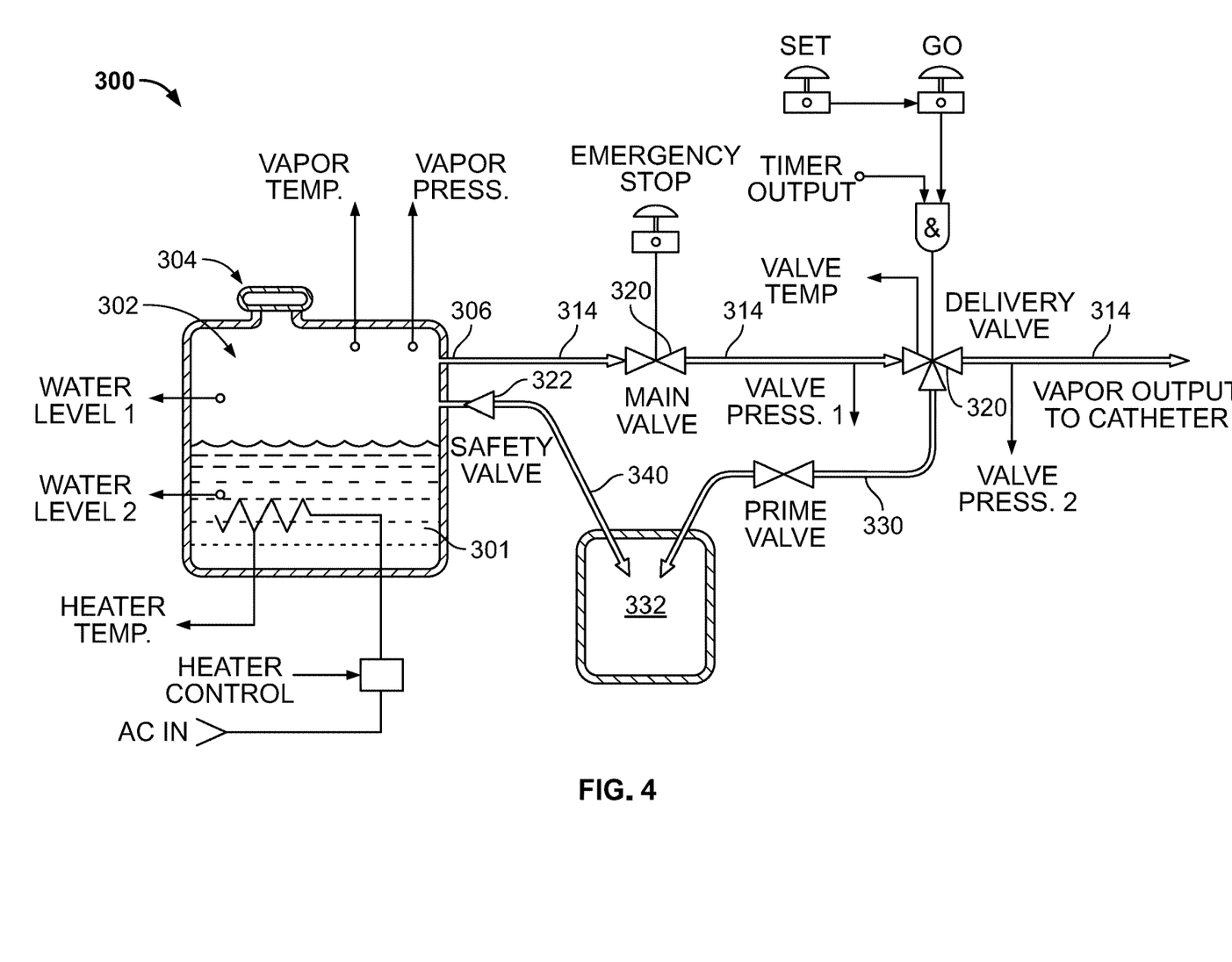
FIG. 4 is a schematic illustration of a vapor generator.

FIG. 4 is a schematic diagram of an energy generator 300 configured as a vapor generator. In embodiments, vapor generator is configured to deliver a controlled dose of vapor to one or more target lung tissues. Vapor generator 300 is adapted to convert a biocompatible liquid 301 (e.g. saline, sterile water or other biocompatible liquid), into a wet or dry vapor, which is then delivered to one or more target tissues. A wet vapor refers to a vapor that contains vaporous forms of the liquid as well as a non-negligible proportion of minute liquid droplets carried over with and held in suspension in the vapor. A dry vapor refers to a vapor that contains little or no liquid droplets. In general, vapor generator 300 is configured to have a liquid capacity between about 1000 to 2500 cc and configured to generate a vapor having a pressure between about 5-100 prig and temperatures between about 100-175° C.

In embodiments, vapor generator 300 is configured as a self-contained, medical-grade generator unit comprising at least a vaporizing unit 302, a fluid inlet 304, and a vapor outlet 306. The vaporizing unit 302 comprises a fluid chamber for containing a fluid 301, preferably a biocompatible, sterile fluid, in a liquid state. In embodiments, vapor outlet 306 is coupled to one or more pipes or tubes, which in turn are placed in fluid communication with an energy delivery catheter 200. Vapor flow from vapor generator 300 to a catheter (and specifically a vapor lumen of said catheter) is depicted as a vapor flow circuit 314 wherein flow of the vapor is indicated by arrows in FIG. 4. In a preferred embodiment, vapor generator is configured to deliver a repeatable dose of vapor to energy delivery catheter 200. Suitable doses of vapor range from 100 to 1000 calories.

Vaporizer unit 302 is configured to heat and vaporize a liquid contained therein. Other components can be incorporated into the biocompatible liquid 301 or mixed into the vapor. For example, these components can be used to control perioperative and/or post procedural pain, enhance tissue fibrosis, and/or control infection. Other constituents, for the purpose of regulating vapor temperatures and thus control extent and speed of tissue heating, can be incorporated; for example, in one implementation, carbon dioxide, helium, other noble gases can be mixed with the vapor to decrease vapor temperatures.

Vaporizing unit 302 is also shown having a fluid inlet 304 to allow liquid 301 to be added to the fluid chamber as needed. Fluid chamber can be configured to accommodate or vaporize sufficient liquid as needed to apply vapor to one or more target tissues. Liquid in vaporizing unit 302 is heated and vaporized and the vapor flows into vapor outlet 306. A number of hollow tubular shafts or pipes are adapted to fluidly connect vapor outlet 306 to the catheter 200.

In embodiments, a flexible hollow tube or umbilical-like cord extends from the generator 300 and terminates in a handle (not shown). The handle is adapted to operatively couple to a variety of types of energy delivery catheters via a hub assembly (such as hub assembly 214 shown in FIG. 5 and discussed herein). In embodiments, the hub assembly or other connecting means is configured to allow for a secure, fluidly sealed, and quick release between the catheter and generator handle. Examples of suitable quick connect and release mechanisms include, without limitation, Luer Lock hub assemblies and fittings.

In embodiments, a catheter and vapor generator are configured to be directly coupled to one another via mating connectors. Vapor delivery is controlled by the generator, a controller external to the generator, or actuating buttons and mechanisms on the catheter itself. For example, the catheter may comprise a handpiece portion to control vapor doses.

Preferably, there is little or no vapor-to-liquid transition during movement of the vapor through vapor flow circuit 314. Vapor flow through vapor flow circuit 314 is unidirectional (in the direction of arrows), accordingly one or more isolation valves 320 are incorporated in vapor flow circuit 314. Isolation valves 320, which are normally open during use of generator 300, serve to minimize vapor flow in a direction opposite that of the vapor flow circuit 314.

A priming line 330, branching from main vapor flow circuit 314, is provided to minimize or prevent undesirable liquid-state water formation during vapor flow through vapor flow circuit 314. Pressure and temperature changes along vapor flow circuit 314 can affect whether the vapor is sustainable in a vapor state or condensed back into a liquid. Priming line 330 is provided to equalize temperatures and/or pressures along vapor flow circuit 314 in order to minimize or prevent undesirable liquid-state transition of the vapor during its progression through vapor flow circuit 314. In one embodiment, an initial "purge" or "priming" procedure can be performed prior to delivery of a therapeutic vapor dose in order to preheat vapor flow circuit 314 thus maintaining a constant temperature and pressure in the main vapor flow circuit 314 prior to delivery of a vapor to the target lung tissue.

As shown in FIG. 4, priming line 330 terminates at evaporator 332, which is adapted to either house undesirable liquid in a collection unit (not shown) located within generator 300. In one embodiment, collection unit is adapted to house the liquid until a user or clinician is able to empty said collection unit. Alternatively, evaporator 332 is configured to evaporate and expel said undesirable liquid into the ambient air. Baffle plates (not shown) or other like means can be incorporated in evaporator 332 to facilitate maximal vapor-to-liquid transition. It should be understood that other suitable evaporator configurations could be included to facilitate vapor-to-liquid transition during a priming procedure of lines in vapor flow circuit 314.

A number of sensors, operatively connected to a controller, can be incorporated into vapor generator 300, for example, in the liquid chamber, or along any point in vapor flow circuit 314. Water level sensors, adapted to monitor the water level in the liquid chamber, can be included. These water level sensors are configured as upper and lower security sensors to sense or indicate when a liquid level in the fluid chamber is below or above a set fluid level. For example, if a water level in the fluid chamber falls below the level of a lower water control sensor, the controller can be configured to interrupt the operation of the vapor generator 300.

In yet another embodiment, pressure sensors, or manometers, can be included in vaporizing unit 302, or at various points along the vapor flow circuit 314, to measure the liquid or vapor pressures at various discrete locations and/or to measure vapor pressures within a defined segment along vapor flow circuit 314. One or more control valves 320 can also be installed at various points in the vapor flow circuit 314 to control vapor flow, for instance, to control or increase the vapor flow or vapor flow rates in vapor flow circuit 314.

In yet another embodiment, a safety valve 322 can be incorporated into the liquid chamber of vaporizing unit 302 and coupled to a vapor overflow line 340 if the need for removing or venting vaporizing unit 302 arises during generator 300 operation.

Although the vapor generator is described above having various specific features, the components and configurations of the vapor generator and catheter systems may vary. Additional vapor ablation systems are described in, for example, U.S. Patent Publication No. 2015/0094607 to Barry et al., and U.S. Pat. No. 7,913,698 to Barry et al., and U.S. Pat. No. 8,322,335 to Barry et al., and U.S. Pat. No. 7,993,323 to Barry et al.

In other embodiments, a condensable vapor is created in the handle portion of the catheter system. Consequently, a separate vapor generator unit is not required. Systems including a resistive heater are described in, for example, U.S. Patent Publication No. 2016/0220297 to Kroon et al. and U.S. Patent Publication No. 2014/0276713 to Hoey et al. Indeed, embodiments of the invention include a wide range of mechanisms to create and transport vapor through the working catheter as described herein.

Vapor Ablation Catheter

Figure 5:
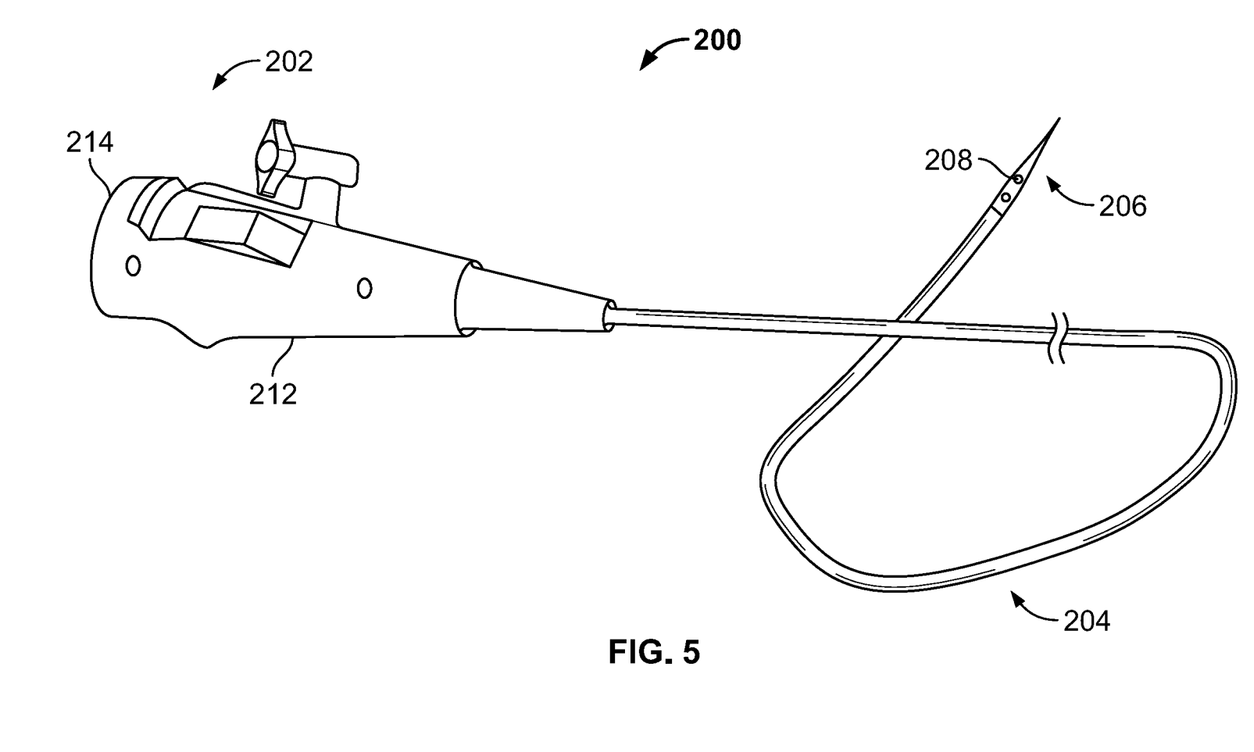
FIG. 5 is an illustration of a vapor ablation catheter.

FIG. 5 illustrates a vapor ablation catheter 200 in accordance with one embodiment of the invention. Catheter 200 is shown having a proximal section 202, intermediate section 204, and distal end section 206. Proximal section 202 can include a handpiece portion 212 and hub 214 which may be connected to the generator as described above. Intermediate section 204 is flexible and continues to distal end section 206. Examples of suitable materials for the catheter shaft include polyimide, PEBAX, silicone, PEEK, and stainless steel braiding.

The distal end section 206 is shown having a pointed tip and a plurality of egress ports 208 for vapor to be directed towards the target tissue. In embodiments, the tip is rigid, sharp, and adapted to penetrate tissue. Examples of suitable materials for the tip of the catheter include stainless steel, Nitinol, and PEEK. At least one egress port 208 is desirable, however, the number of egress ports may range from 1-20, and more preferably 6-12.

The shape of the egress port is shown as a circle. However, the shape and size of the egress ports may vary. In embodiments, the egress port has a circular shape and a diameter in the range of 0.1 to 2 mm.

FIG. 5 shows the egress ports 208 on one lateral surface, face, side, or facet of the tip. The vapor may thus be aimed in solely one direction. However, in other embodiments, the egress ports are spaced about the circumference of the distal end section such that the vapor may be directed radially in all directions from the shaft. In yet other embodiments, the egress port(s) are located on the end of the catheter tip and send the vapor in an axial direction.

Additional examples of vapor delivery catheter configurations are described in the literature. Another example of a vapor catheter having components and structures which may be combined with the subject invention is described in U.S. Pat. No. 8,444,636 to Shadduck and Hoey; and U.S. Patent Publication No. 2014/0025057 to Hoey and Shadduck. The catheter and tip configuration may vary widely and the invention is only intended to be limited as recited in the appended claims.

Asthma Treatment

Figure 6A:
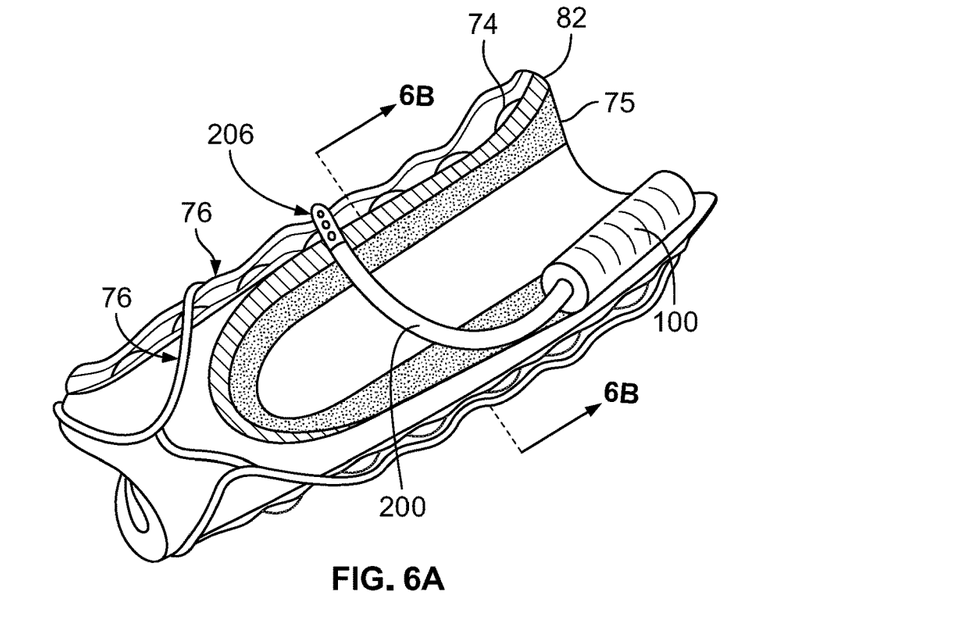
FIG. 6A is an illustration of a vapor ablation catheter advanced to a target tissue for treating asthma.

FIG. 6A illustrates use of a vapor ablation catheter 200 to treat an asthmatic airway 82. The airway is shown in a constricted state due to the contraction of smooth muscles 74, and the condition is further exacerbated by the presence of an increased mucus layer 75.

FIG. 6A also shows catheter 200 having been advanced from the bronchoscope 100. Distal end section 206 is shown passing through the airway wall 82, between smooth muscle segments 74, and facing towards or in contact with nerve portion 76.

In embodiments, the catheter distal section is advanced through a surgically created opening, passageway, or ancillary appliance, channel or instrument extending through the airway wall to the target tissue. Techniques and instruments for creating passageways and installing working tubes through the airway wall, and for performing procedures through the passageways, are described in, for example, U.S. Pat. Nos. 8,409,167 and 8,709,034.

Figure 6B:
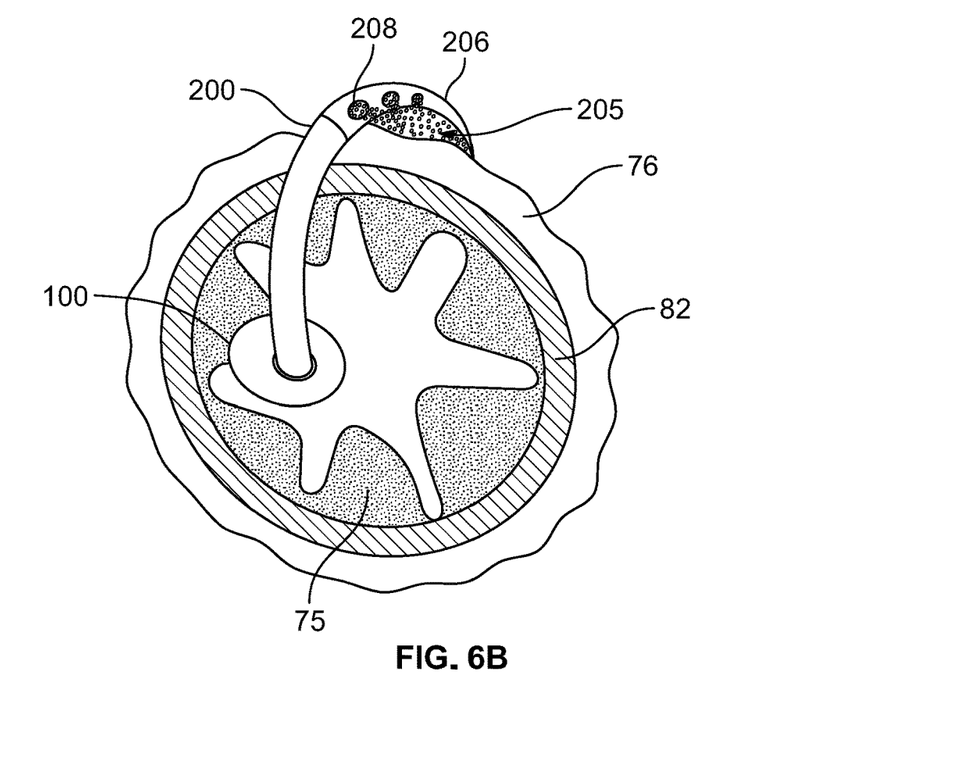
FIG. 6B is a cross sectional view of the airway anatomy and vapor ablation catheter shown in FIG. 6A taken along line 6B-6B.

FIG. 6B is a cross section illustration of FIG. 6A, taken along line 6B-6B. Distal end section 206 of the catheter is shown advanced outside of the airway, and adjusted to face nerve portion 76. Egress ports 208 are shown aimed or directed towards the exterior surface of the nerve 76, and in some embodiments, the smooth muscle.

Vapor 205 is shown delivered from the egress ports 208 towards the nerve 76, and, with reference again to FIG. 6A, the smooth muscle 74 surrounding the outside of the airway. As mentioned herein, and without intending to be bound to theory, heating the nerve and smooth muscles surrounding the airway prevents the narrowing of the airway characteristic of an asthma attack.

It should also be appreciated that the embodiment shown in FIG. 6B demonstrates the distal end 206 being located in close proximity (e.g., within 5 mm) and perhaps even making contact with the exterior surface of the nerve 76. The vapor 205 is directed towards the target and, due to its gaseous state, tends to follow the target airway boundary, creating a safer, faster, and more precise energy delivery than previous methods (e.g., a heat source placed against the interior surface of the airway wall 82).

Figure 6C:
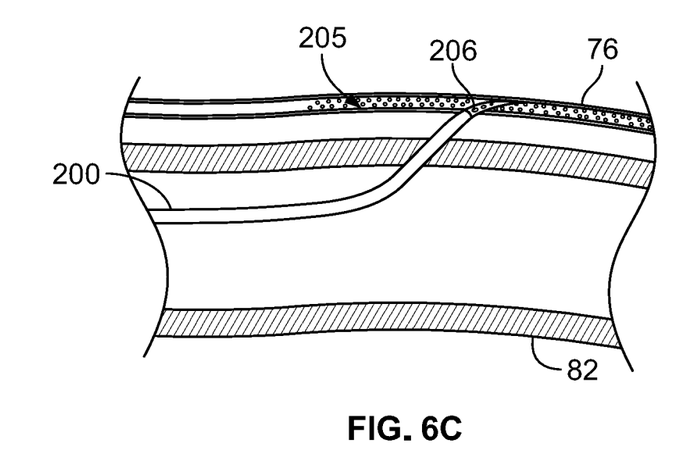
FIGS. 6C, 6D show a catheter delivering energy into (or within) a nerve and smooth muscle, respectively.
Figure 6D:
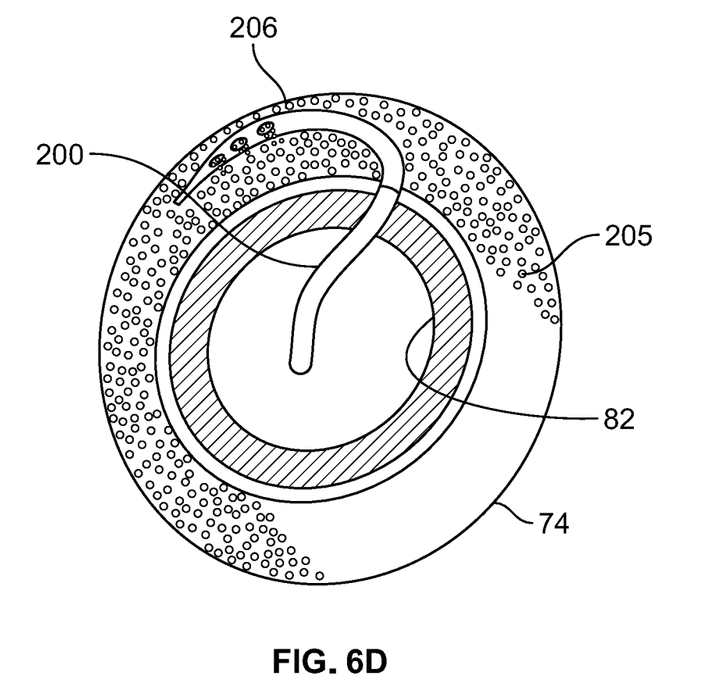

FIG. 6C and FIG. 6D show the catheter 200 delivering energy into (or within) the nerve 76 and smooth muscle 74, respectively. In embodiments, catheter distal section 206 has a needle-like configuration or otherwise sharp tip to penetrate and enter the targeted tissues. The vapor 205 is shown moving, or otherwise flowing through the targeted tissue and follows the boundary of the target tissue because of the presence of higher density cells on the margin or perimeter of the target tissue. The vapor thus moves quickly within the target tissue, and along its boundary, causing thermal ablation as described herein.

In embodiments, a method includes dispersing a vapor through a volume of a first tissue (or filling the first tissue structure with the vapor) with a dose sufficient to render the target tissue non-functional, or to destroy the tissue. The amount and type of energy (flow rate, composition, temperature) may be controlled by the system and based on the characteristics of the target tissue including volume, mass, density, location, and type of tissue. Example quantities or amounts of energy range from 10 to 2000 calories, and in embodiments 100 to 1000 calories.

Assessing Catheter Location

In embodiments, as described further herein, methods include assessing the location of the distal end section of the catheter to determine whether the distal section of the catheter is in contact (or otherwise properly located) relative to the target tissue. Nonlimiting examples of target tissue include nerves, smooth muscle, airway tissue, blood vessels as well as tumors, infected or diseased tissues, lymph nodes and tissue growths whether cancerous or benign.

Techniques for confirming or assessing the position of the distal end section may vary. In embodiments, assessing the location of the distal end section may be performed using noninvasive imaging means, and guidance software. Non-limiting examples of guidance techniques include video or fluoroscopy based tracking and guidance, and electromagnetic based guidance via use of transponders or other sensors or transmitters. Systems may be employed to track the location of the distal end section relative to previously obtained image data of the patient. Examples of tracking and guidance techniques are described in U.S. Pat. No. 7,233,820 to Gilboa; U.S. Pat. No. 7,756,563 to Higgins et al.; U.S. Pat. No. 7,889,905 to Higgins et al.; U.S. Pat. No. 9,265,468 to Rai et al.; and U.S. Patent Publication No. 20160180529 to Rai et al. See, e.g., the Superdimension™ Navigation System, manufactured by Medtronic (Minneapolis, Minn.), and the Archimedes™ System, manufactured by Broncus Medical, Inc., (San Jose, Calif.).

Additionally, in embodiments, the physician can preoperatively plan one or more routes through the airways to the target tissue. An entire pathway or route may be planned from the mouth or nasal passageway, through the airways, and to the target tissue outside of the airway. Then, the pre-planned or pre-determined route may be used during the procedure to guide the physician. One of the above described guidance techniques can be used to assess the location of the catheter as it is advanced into the target position. Examples of a route planning techniques are described in U.S. Pat. No. 9,037,215 and U.S. Patent Publication No. 2009/0156895, both to Higgins et al. See also the LungPoint® Planner, manufactured by Broncus Medical, Inc., (San Jose, Calif.).

Additionally, in embodiments, automatic and semi-automatic compiling and evaluation of lung image data, image reconstruction, and display is performed. See, e.g., U.S. Pat. No. 9,037,215 to Higgins et al., and U.S. Patent Publication Nos. 2009/0156895 and 2010/0310146 both to Higgins et al., and 2014/0275952 to Monroe et al.

Physical assessment of the position of the catheter relative to the target nerve may also be performed, for example, via empirical techniques including observing movement of the nerve/airway and/or measuring nerve activity as the catheter tip is moved into and out of contact with the nerve (e.g., touching, probing, or interrogating).

Figure 7:
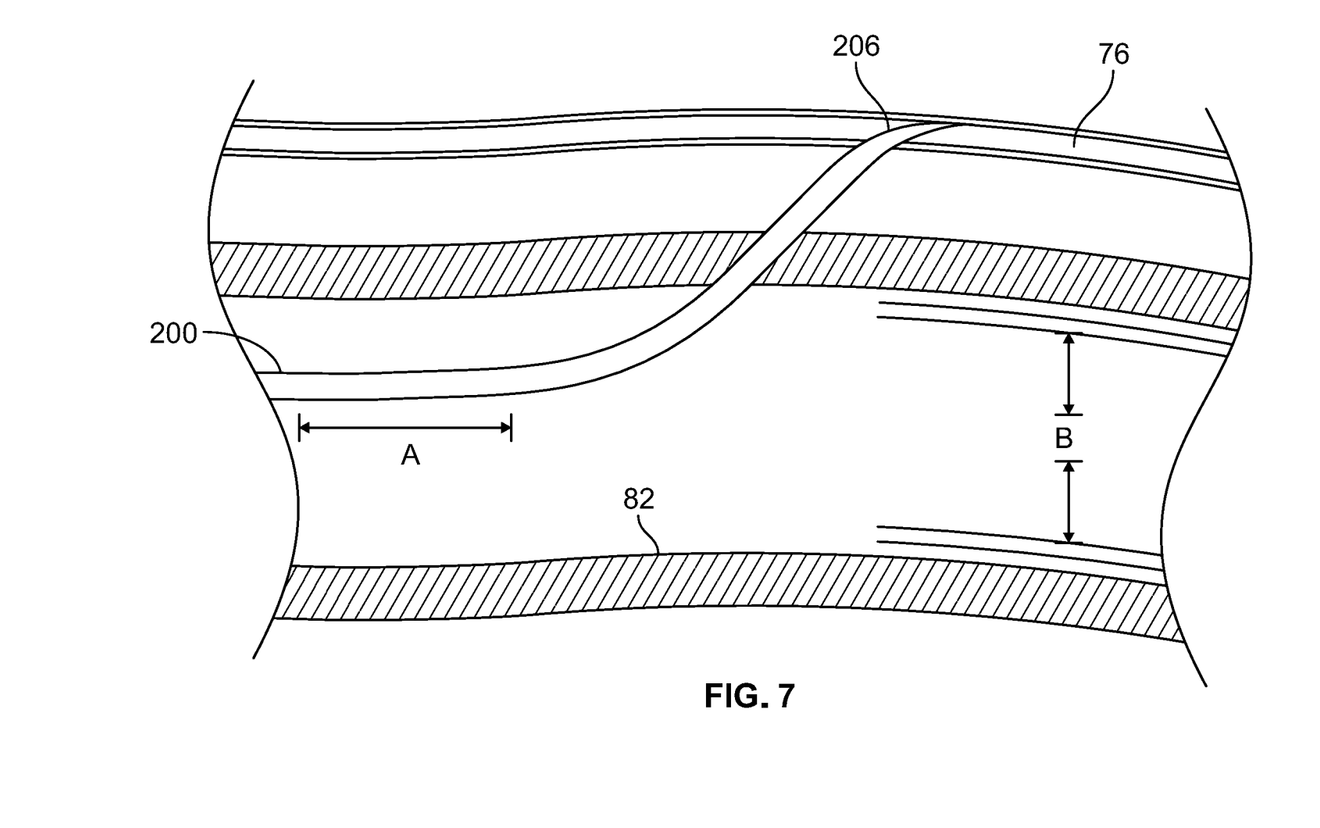
FIG. 7 is an illustration of a catheter being advanced into an extra-airway target tissue, resulting in motion of the airway.

In embodiments, and with reference to FIG. 7, the distal end section 206 of the catheter 200 is shown advanced through an opening in the airway wall 82, and a needle tip inserted into the nerve 76. The physician may visually observe movement (B) of the airway wall in response to advancement (A) of the catheter 200 towards the nerve 76. Airway spasms may be visible by a bronchoscope positioned in the airway. Movement or spasms can be indicative of the tip 206 penetrating or making contact with the nerve.

Additionally, external sensors may interrogate or confirm contact between the distal tip and the nerve or smooth muscle. Such tests record or sense nerve activity or electrical activity in a minimally or noninvasive manner. Nonlimiting examples of external sensors include electromyography (EMG) sensors and systems. In embodiments, a surface-type EMG sensor is affixed to the skin of the patient to monitor nerve activity.

Candidate Nerve Screening Method

Figure 8:
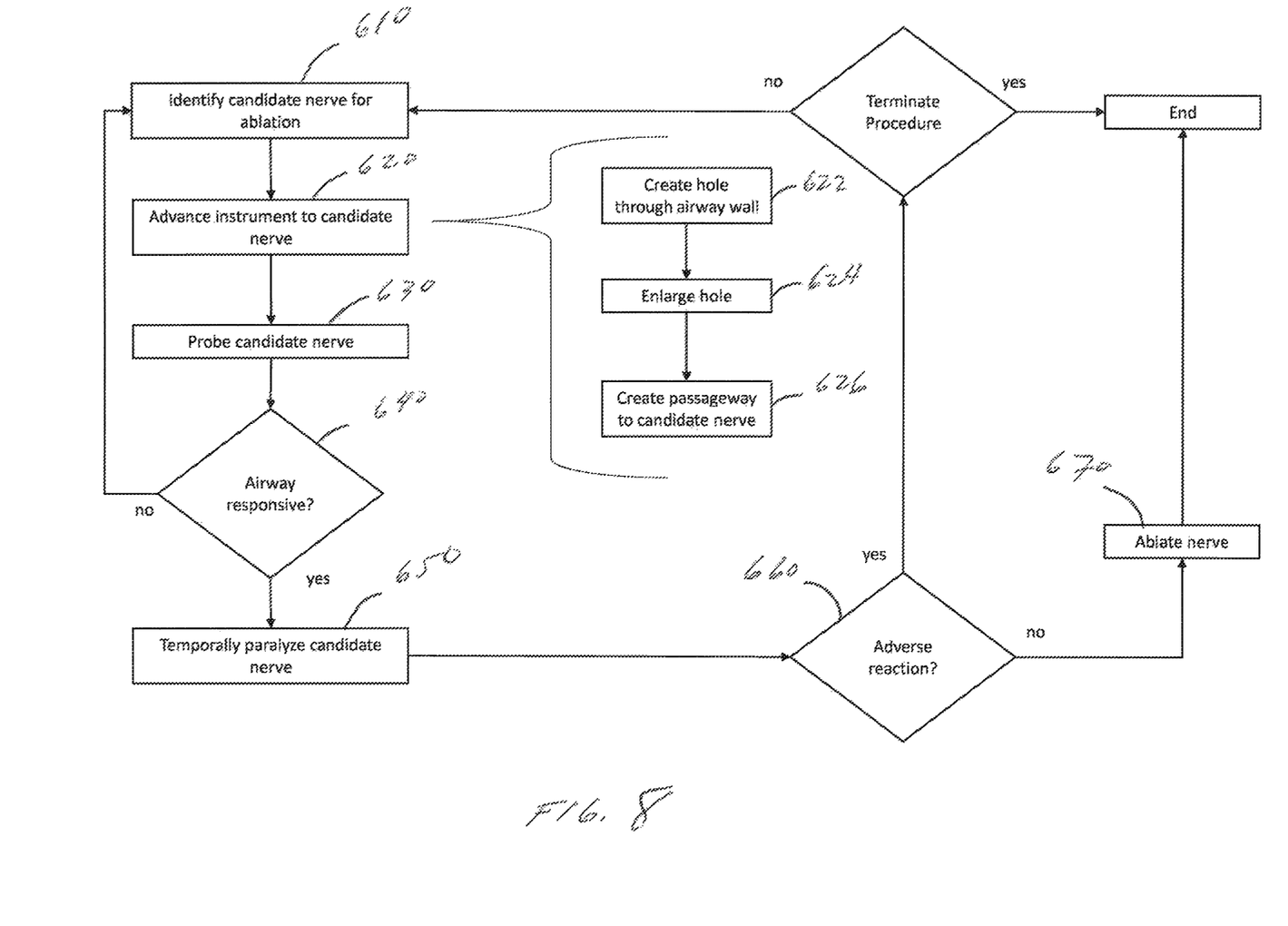
FIG. 8 is a flowchart of a screening method for a target nerve to ablate for the treatment of lung inflammatory disease.

FIG. 8 is a flowchart describing a method 600 for identifying a target nerve for ablating for the treatment of lung inflammatory disease such as COPD and asthma.

Step 610 states to identify the candidate nerve for ablation. An example of a candidate nerve to ablate is the pulmonary parasympathetic nerve (PPN). Endoscopy or noninvasive means such as MRI may be applied to view and identify the target. Further, the physician can locate the PPN radially along the airway (e.g. at 10 o'clock or 2 o'clock as one looks down the airway). The PPN is visible under MRI because the nerve may be 2 to 3 mm in diameter at the point where the physician would desire to ablate.

Optionally, planning software is employed to visualize the candidate nerve in renderings of the patients lungs (e.g., the nerve may be superimposed onto a 3D reconstruction of the airway tree). Examples of route planning techniques are described in U.S. Pat. No. 9,037,215 and U.S. Patent Publication No. 2009/0156895, both to Higgins et al. See also the LungPoint® Planner, manufactured by Broncus Medical, Inc., (San Jose, Calif.).

Step 620 states to advance an instrument or tool to the candidate nerve.

In embodiments, and with reference to step 622, an opening through the airway wall is created. This step may be performed using a needle catheter, or a sharpened tip of the instrument or tool.

Optionally, the hole may be enlarged (step 624) using a dilator or expandable member.

Step 626 states to create the passageway to the candidate nerve. This step may be performed by advancing the instrument through the hole and towards the target tissue outside of the airway. For example, the needle catheter or needle sheath may be advanced through the hole and toward the candidate nerve. Additionally, a tunneling tool can be advanced through the tissue to create a passageway sufficient in size to accommodate the forthcoming procedural steps. A conduit or channel may be installed, serving to provide an open access channel to the nerve. Indeed, a number of techniques and instruments for creating passageways through the airway wall and smooth muscles, and for performing procedures through the passageways, may be used in combination with the invention. Examples are described in U.S. Pat. Nos. 8,409,167 and 8,709,034.

Confirming the location of the tool and instrument is also desired. Techniques for confirming or assessing the position of the distal end section of the tool may be performed using noninvasive imaging means, and guidance software. Non-limiting examples of guidance techniques include video or fluoroscopy based tracking and guidance, and electromagnetic based guidance including transponders or other sensors or transmitters. Systems may be employed to track the location of the distal end section relative to previously obtained image data of the patient. Examples of tracking and guidance techniques are described in U.S. Pat. No. 7,233,820 to Gilboa; U.S. Pat. No. 7,756,563 to Higgins et al.; U.S. Pat. No. 7,889,905 to Higgins et al.; U.S. Pat. No. 9,265,468 to Rai et al.; and U.S. Patent Publication No. 20160180529 to Rai et al. See, e.g., the Superdimension™ Navigation System, manufactured by Medtronic (Minneapolis, Minn.), and the Archimedes™ System, manufactured by Broncus Medical, Inc., (San Jose, Calif.).

Step 630 states to probe the candidate nerve. As described herein, this step may be carried out using various means. In embodiments, the distal end of the instrument or tool (e.g., a small gauge needle) is urged into the tissue.

Step 640 states to query whether the airway is responsive to the probing step 630. In embodiments, the physician visually monitors the airway for contraction as the nerve is probed.

Additionally, assessment of the candidate nerve may be performed via empirical techniques including observing movement of the nerve/airway and/or measuring nerve activity as the catheter tip is moved into and out of contact with the nerve (namely, hitting or probing). As described above, external sensors may interrogate or confirm contact between the distal tip and the nerve or smooth muscle. Such tests record or sense nerve activity or electrical activity in a minimally or noninvasive manner. Nonlimiting examples of external sensors include electromyography (EMG) sensors and systems. In embodiments, a surface-type EMG sensor is affixed to the skin of the patient to monitor nerve activity. Measuring nerve activity is desirable when direct visualization is impractical due to bleeding in the field of view of the bronchoscope.

Should probing the candidate nerve not generate airway responsiveness, the physician has the option to identify another candidate nerve and repeat the process as indicated in FIG. 8.

Step 650 states for the physician to temporarily paralyze the candidate nerve should the airway be responsive to the probing step. Step 650 can be performed using various techniques or tools. For example, temporarily blocking may be performed by injecting local anesthetics such as bupivacaine, levobupivacaine, or ropivacaine.

In embodiments, the nerve is temporarily frozen using cryo.

In embodiments, the nerve is paralyzed by mechanical action (e.g., pinching using a temporary clip or restrictor).

Step 660 states to query for an adverse reaction while the candidate nerve is temporarily paralyzed. Step 660 may be performed by visually monitoring the patient for unintended consequences or collateral damage to nerves and tissues not targeted. If an adverse reaction is observed during the temporarily blocking step, the procedure may be terminated or another candidate nerve may be identified. And the process is repeated returning to step 610.

If, on the other hand, an adverse reaction is not observed, the physician may characterize the candidate nerve as the target nerve to be ablated or otherwise permanently blocked.

Step 670 states to ablate the nerve. If temporarily paralyzing the nerve is observed to be safe and, more preferably, to also provide a clinical benefit to the patient, the physician ablates the nerve at the site where the paralyzing step occurred. In embodiments, the physician follows the previous path used during the paralyzing step, and applies energy directly to the nerve. For reasons described herein, applying energy directly to the nerve is preferred to applying energy indirectly to the nerve (e.g., applying heat to the inner surface of the airway wall, and raising the temperature of the nerve via thermal conduction through the airway wall, through the smooth muscle, and ultimately to the nerve). Precise direct ablation limits the inadvertent ablation of pulmonary vessels and other tissue in the vicinity of the target nerve.

The step of ablation may be carried out using a wide range of techniques. Exemplary modalities of ablation include use of a condensable vapor, RF, microwave, or cryo.

In a preferred embodiment, ablation is carried out using a thermal vapor ablation catheter.

Alternative Embodiments

The invention has been discussed in terms of certain embodiments. One of skill in the art, however, will recognize that various modifications may be made without departing from the scope of the invention. For example, numerous variations, changes, and substitutions will now occur to those skilled in the art without departing from the invention. Moreover, while certain features may be shown or discussed in relation to a particular embodiment, such individual features may be used on the various other embodiments of the invention.

The invention claimed is:

1. A method of screening for a target nerve to ablate in a lung of a patient for the treatment of COPD or asthma, the method comprising:
   selecting a candidate nerve in the lung to temporarily paralyze;
   advancing an instrument along an airway in the lung and into the vicinity of the candidate nerve;
   interrogating the candidate nerve, wherein the step of interrogating the nerve is performed by probing the candidate nerve by pushing a needle-like sharp tip against the candidate nerve and evaluating contraction of the airway,
   wherein the interrogating step comprises observing whether an airway controlled by the candidate nerve moves, and
   wherein the observing is performed by direct visualization of the airway motion arising from physically pushing on the candidate nerve with the sharp tip;
   temporarily paralyzing the candidate nerve with the instrument if airway contraction arose from the interrogating step; and
   monitoring the patient for a reaction during the temporarily paralyzing step.

2. The method of claim 1, further comprising selecting an alternate candidate nerve if an adverse reaction is observed during the monitoring step, and temporarily paralyzing the alternate candidate nerve.

3. The method of claim 1 wherein the temporarily paralyzing step comprises injecting a local anesthetic into the candidate nerve.

4. The method of claim 3 wherein the local anesthetic is one selected from the group consisting of bupivacaine, levobupivacaine, and ropivacaine.

5. The method of claim 1 wherein the temporarily paralyzing step comprises freezing.

6. The method of claim 1 further comprising identifying the candidate nerve as the target nerve to be ablated if an adverse reaction is not observed during the observing step.

7. The method of claim 6 further comprising directly ablating the target nerve.

8. The method of claim 7 wherein the ablation is performed using a condensable vapor.

9. The method of claim 8 wherein the condensable vapor is generated and delivered from a vapor generator system comprising a controller having a graphical user interface, an elongate flexible catheter, and a handpiece for activating the vapor delivery.

10. The method of claim 9 wherein the catheter includes an expandable distal region.

11. The method of claim 1 wherein the nerve is the pulmonary parasympathetic nerve (PPN).

12. The method of claim 1 wherein the probing is applied at the 10 or 2 o'clock position along the airway.

* * * * *